US010524688B2

(12) United States Patent
Kolipaka et al.

(10) Patent No.: US 10,524,688 B2
(45) Date of Patent: Jan. 7, 2020

(54) HYDRAULICALLY-POWERED AND HYBRID HYDRAULIC-PNEUMATIC SYSTEMS AND METHODS FOR ACHIEVING MAGNETIC RESONANCE ELASTOGRAPHY

(71) Applicant: OHIO STATE INNOVATION FOUNDATION, Columbus, OH (US)

(72) Inventors: Arunark Kolipaka, Dublin, OH (US); John W. Arnold, New Philadelphia, OH (US); F. Paul Lee, Wooster, OH (US); Richard D. White, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 331 days.

(21) Appl. No.: 15/524,948

(22) PCT Filed: Nov. 13, 2015

(86) PCT No.: PCT/US2015/060717
§ 371 (c)(1),
(2) Date: May 5, 2017

(87) PCT Pub. No.: WO2016/077776
PCT Pub. Date: May 19, 2016

(65) Prior Publication Data
US 2017/0332937 A1 Nov. 23, 2017

Related U.S. Application Data

(60) Provisional application No. 62/079,831, filed on Nov. 14, 2014.

(51) Int. Cl.
| A61B 5/055 | (2006.01) |
| A61B 5/00 | (2006.01) |
| G01R 33/563 | (2006.01) |

(52) U.S. Cl.
CPC .......... *A61B 5/055* (2013.01); *A61B 5/0051* (2013.01); *G01R 33/56358* (2013.01)

(58) Field of Classification Search
CPC .. A61B 5/055; A61B 5/0051; G01R 33/56358
See application file for complete search history.

(56) References Cited

U.S. PATENT DOCUMENTS

| 4,472,628 A | 9/1984 | Whitten |
| 5,265,612 A | 11/1993 | Sarvazyan et al. |

(Continued)

FOREIGN PATENT DOCUMENTS

DE          3139399       4/1983

OTHER PUBLICATIONS

International Search Report and Written Opinion for Application No. PCT/US2013/040272 dated Sep. 5, 2013 (7 pages).

(Continued)

*Primary Examiner* — Tse W Chen
*Assistant Examiner* — Jason M Ip
(74) *Attorney, Agent, or Firm* — Michael Best & Friedrich LLP

(57) ABSTRACT

Systems and methods are described for inducing tissue vibration for magnetic resonance elastography is described. The system includes a hydraulic drive component that is mechanically linked to a pneumatic drive component. The pneumatic drive component is pneumatically linked to a passive pneumatic actuator component that is positionable on a patient proximate to a target tissue. Alternating linear movement of an actuator piston within the passive actuator component induces vibration of the target tissue. The frequency of the alternating linear movement of the actuator piston within the passive pneumatic actuator component is controlled by adjusting how fluid is pumped in the hydraulic drive component.

18 Claims, 8 Drawing Sheets

(56) References Cited

U.S. PATENT DOCUMENTS

| | | | |
|---|---|---|---|
| 5,540,052 | A | 7/1996 | Sieke et al. |
| 7,034,534 | B2 | 4/2006 | Ehman et al. |
| 7,467,007 | B2 | 12/2008 | Lothert |
| 7,731,661 | B2 | 6/2010 | Salcudean et al. |
| 9,295,407 | B2 | 3/2016 | Kolipaka et al. |
| 2009/0209847 | A1 | 8/2009 | Li |
| 2010/0045289 | A1 | 2/2010 | Bronskill et al. |
| 2010/0241012 | A1 | 9/2010 | Yin et al. |
| 2011/0025333 | A1 | 2/2011 | Ehman et al. |
| 2011/0141102 | A1 | 6/2011 | Skinner et al. |
| 2012/0053450 | A1 | 3/2012 | Salcudean |
| 2013/0303882 | A1 | 11/2013 | Kolipaka et al. |

OTHER PUBLICATIONS

European Patent Office Extended Search Report for Application No. 13787687.6 dated Dec. 14, 2015 (9 pages).

International Search Report and Written Opinion for Application No. PCT/US2015/060717 dated Feb. 9, 2016 (11 pages).

International Search Report and Written Opinion for Application No. PCT/US2016/027311 dated Jul. 12, 2016 (14 pages).

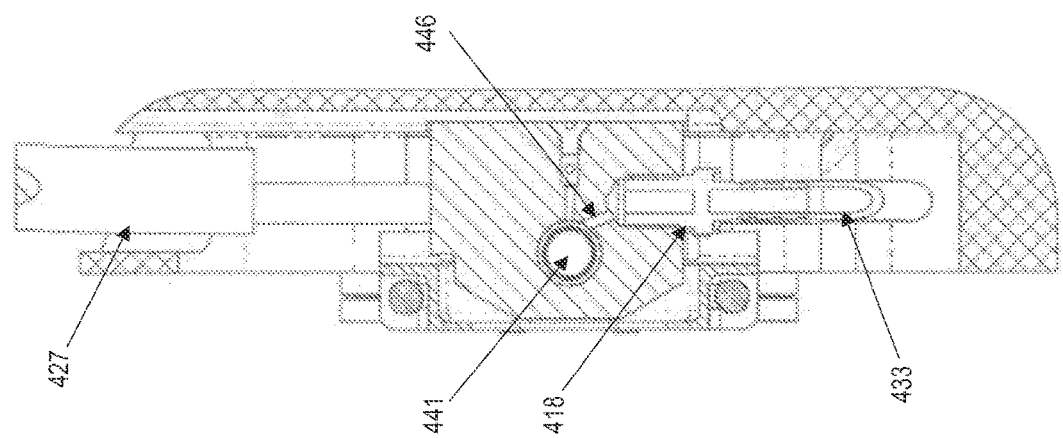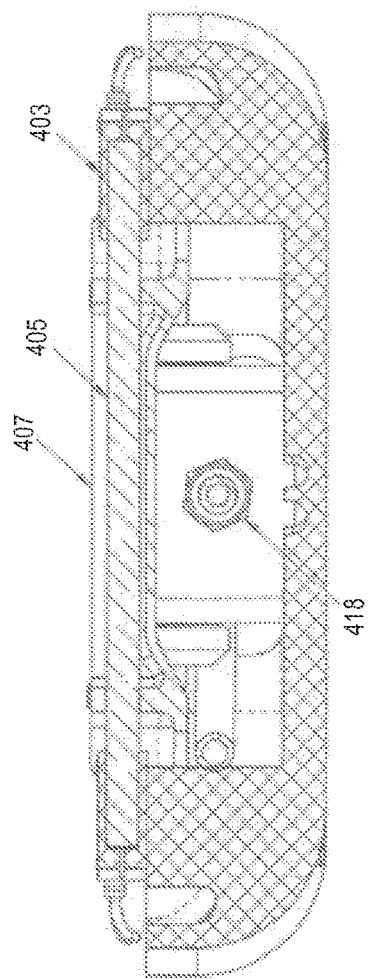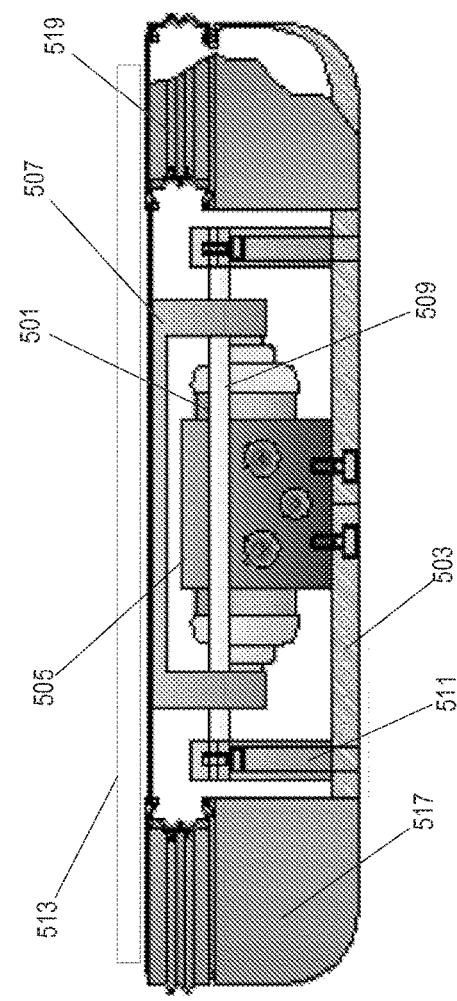

HYDRAULICALLY-POWERED AND HYBRID HYDRAULIC-PNEUMATIC SYSTEMS AND METHODS FOR ACHIEVING MAGNETIC RESONANCE ELASTOGRAPHY

CROSS-REFERENCE TO RELATED APPLICATION(S)

This application is a U.S. national stage entry of International Patent Application No. PCT/US2015/060717, filed on Nov. 13, 2015, and entitled "HYDRAULICALLY-POWERED AND HYBRID HYDRAULIC-PNEUMATIC SYSTEMS AND METHODS FOR ACHIEVING MAGNETIC RESONANCE ELASTOGRAPHY," which claims the benefit of U.S. Provisional Patent Application No. 62/079,831, filed on Nov. 14, 2014, and entitled "HYDRAULICALLY-POWERED AND HYBRID HYDRAULIC-PNEUMATIC SYSTEMS AND METHODS FOR ACHIEVING MAGNETIC RESONANCE ELASTOGRAPHY," the entire contents of each of which are fully incorporated herein by reference.

BACKGROUND

Embodiments of the invention relate to a non-invasive medical imaging technique, such as magnetic resonance elastography ("MRE"), used to measure stiffness of tissues.

Current MRE technology, including systems that employ an acoustic driver or a purely pneumatic driver system, are generally limited to low frequency vibrations (e.g., 100 Hz or less). Because the wavelengths from the low frequency vibrations are smaller than the dimensions of some tissues, current pneumatic systems can be used to generate stable stiffness maps for some organs such as the liver, which might then be used to diagnose liver diseases, such as liver fibrosis. These limitations similarly affect the ability to use MRE technologies to generate stable stiffness maps for organs such as the heart, prostate, pancreas, spleen, eye, etc.

SUMMARY

Some systems and methods described herein provide a hydraulically-powered magnetic resonance elastography ("MRE") vibration device used in conjunction with a magnetic resonance imaging ("MRI") scanner that uses an inversion to generate stable stiffness maps for various organs. The vibration device generates high frequency vibrations, up to approximately 1000 Hz, which non-invasively penetrate deeper into tissue than current MRE technology to identify a disease and diagnose the state of the disease for various organs of a human or an animal body.

In one embodiment, the invention provides a hydraulically-powered system used in conjunction with a magnetic resonance imaging ("MRI") device and an inversion to achieve magnetic resonance elastography ("MRE") generated stiffness maps. The hydraulically-powered system includes an application component, a driving component, and a plurality of hoses connecting the application component to the driving component. The application component (also referred to as a passive driver, a passive device, or a passive actuator) includes a piston rod assembly, and is positioned on a surface of a body to cause biological tissues under study to vibrate synchronized with the phase of the MRI signal of the MRI device. The driving component includes a processing unit, a memory storing data and firmware executable by the processing unit, and at least one pump or a combination of a pump and a valve. The driving component is configured to operate the application component at a controlled frequency, amplitude, and phase.

Other systems and methods described herein provide a hybrid pneumatic-hydraulic drive system for MRE procedures. Some such systems include a controlled hydraulic drive mechanism, a passive pneumatic actuator, and a hydraulic-pneumatic converter for translating hydraulic-control to the pneumatic actuator system that induces vibrations in the patient tissue. Utilizing hydraulic mechanisms provides for a higher degree of reliable control at higher frequencies while employing a pneumatic actuator to induce vibration in the patient tissue reduces (or eliminates) the need for high-pressurized fluids in the MRI environment and simplifies the procedure for changing or replacing the passive actuator component.

Accordingly, in some embodiments, the invention provides a system for inducing tissue vibration for magnetic resonance elastography. The system includes a hydraulic drive component that is mechanically linked to a pneumatic drive component. The pneumatic drive component is pneumatically linked to a passive pneumatic actuator component that is positionable on a patient proximate to a target tissue. Alternating linear movement of an actuator piston within the passive actuator component induces vibration of the target tissue. The frequency of the alternating linear movement of the actuator piston within the passive pneumatic actuator component is controlled by adjusting how fluid is pumped in the hydraulic drive component.

In some embodiments, the invention provides a system for inducing tissue vibration for magnetic resonance elastography including a hydraulic drive component, a pneumatic drive component, and a passive actuator component. The hydraulic drive component includes a linearly movable hydraulic piston stage enclosed in a hydraulic drive housing, a fluid pump, and a controllable valve system. The controllable valve system is configured to alternatingly pump fluid into the hydraulic drive housing on a first side of the hydraulic piston stage causing the hydraulic piston stage to move in a first linear direction relative to the hydraulic drive housing and on a second side of the hydraulic piston stage causing the hydraulic piston stage to move in a second linear direction relative to the hydraulic drive housing. The second linear direction relative to the hydraulic drive housing is opposite the first linear direction relative to the hydraulic drive housing. The pneumatic drive component includes a pneumatic piston stage enclosed in a pneumatic drive housing. The pneumatic piston stage is mechanically linked to the hydraulic piston stage such that movement of the hydraulic piston stage in the first linear direction relative to the hydraulic drive housing causes movement of the pneumatic piston stage in a first linear direction relative to the pneumatic drive housing and movement of the hydraulic piston stage in the second linear direction relative to the hydraulic drive housing causes movement of the pneumatic piston stage in a second linear direction relative to the pneumatic drive housing. The second linear direction relative to the pneumatic drive housing is opposite the first linear direction relative to the pneumatic drive housing. The passive actuator component is positionable proximate to a target tissue and includes a linearly movable actuator piston assembly enclosed in an actuator housing. The actuator housing is pneumatically coupled to the pneumatic drive component such that movement of the pneumatic piston stage in the first linear direction relative to the pneumatic drive housing causes movement of the actuator piston assembly in a first linear direction relative to the actuator housing and movement of the pneumatic piston stage in the second linear direction relative to the pneumatic drive housing causes movement of the actuator piston assembly in a second linear direction relative to the actuator housing. The second linear direction relative to the actuator housing is opposite the first linear direction relative to the actuator housing.

In other embodiments, the invention provides a method of inducing tissue vibration for magnetic resonance elastography. A passive pneumatic actuator component is positioned on an imaging subject proximate to a target tissue. The passive actuator component includes linearly moveable actuator piston assembly enclosed in an actuator housing. Fluid is alternatingly pumped into a hydraulic drive housing on a first side of a hydraulic piston assembly and on a second side of the hydraulic piston assembly. Pumping fluid into the hydraulic drive housing on the first side of the hydraulic piston assembly causes the hydraulic piston assembly to move in a linear direction opposite the first side of the hydraulic piston assembly. Pumping fluid into the hydraulic drive housing on the second side of the hydraulic piston assembly causes the hydraulic piston assembly to move in a linear direction opposite the second side of the hydraulic piston assembly. A mechanical linkage between the hydraulic piston assembly and a pneumatic piston assembly positioned within a pneumatic drive housing causes the pneumatic piston assembly to move in a first linear direction relative to the pneumatic drive housing in response to linear movement of the hydraulic piston assembly in the linear direction opposite the first side of the hydraulic piston assembly. The mechanical linkage also causes the pneumatic piston assembly to move in a second linear direction relative to the pneumatic drive housing in response to linear movement of the hydraulic piston assembly in the linear direction opposite the second side of the hydraulic piston assembly. A pneumatic linkage between the pneumatic drive housing and the passive actuator component causes a pneumatic gas to be forced from the pneumatic drive housing on a first side of the pneumatic piston stage into the actuator housing on a first side of the actuator piston assembly in response to movement of the pneumatic piston stage in the first linear direction relative to the pneumatic drive housing. The pneumatic linkage also causes the pneumatic gas to be forced from the pneumatic drive housing on a second side of the pneumatic piston stage into the actuator housing on a second side of the actuator piston assembly in response to movement of the pneumatic piston stage in the second linear direction relative to the pneumatic drive housing. Forcing the pneumatic gas into the actuator housing on the first side of the actuator piston assembly causes the actuator piston assembly to move in a linear direction opposite the first side of the actuator piston. Forcing the pneumatic gas into the actuator housing on the second side of the actuator piston assembly causes the actuator piston assembly to move in a linear direction opposite the second side of the actuator piston. Therefore, alternatingly pumping the fluid into the hydraulic drive housing on the first side of the hydraulic piston assembly and on the second side of the hydraulic piston assembly causes alternating linear movement of the actuator piston assembly within the passive pneumatic actuator component.

BRIEF DESCRIPTION OF THE DRAWINGS

FIG. 4F is a fourth cross-sectional view of the passive actuator component of FIG. 4A.

FIG. 4G is a final cross-sectional view of the passive actuator component of FIG. 4A.

FIG. 5 is a partially cut-away view of an exterior housing for a passive actuator component for use in the system of FIG. 1.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
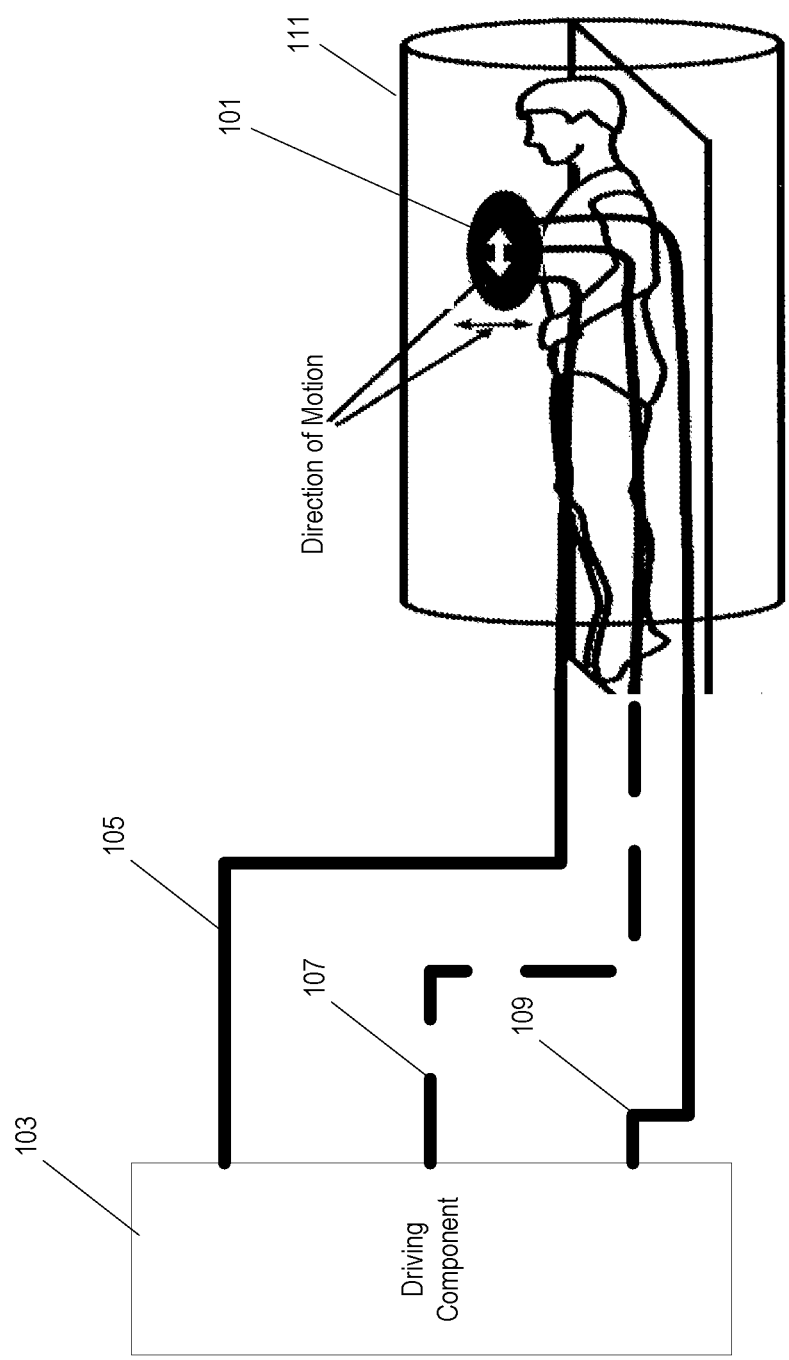
FIG. 1 is a schematic diagram of an actuator and drive system used in conjunction with a magnetic resonance imaging ("MRI") device for performing magnetic resonance elastography ("MRE").

FIG. 1 illustrates an example of a hydraulically-powered magnetic resonance elastography ("MRE") system including an application component 101, a driving component 103, and a plurality of hoses 105, 107, 109 connecting the application component 101 to the driving component 103. When a patient is placed in an MRI environment 111, the application component 101 (also referred to as a passive driver, a passive device, or a passive actuator) is adhered to the surface of a patient's body and generates vibrations perpendicular to the tissue surface or shear vibrations along the tissue surface. To prevent interference with the MRI system, the passive driver 101 is constructed of non-metallic/MR compatible components. However, in some constructions, the passive driver 101 includes a limited number of non-ferromagnetic metallic components.

The driving component 103 (also referred to as an active driver) includes pump mechanisms for driving the hydraulic system. As some of these components may be constructed of metal (including ferromagnetic metals), the driving component 103 is positioned outside of the MRI environment/scanning room. As described in detail below, the driving component 103 operates a hydraulic pumping system to control the frequency, displacement amplitude, and phase of the passive driver 101.

The system of FIG. 1 undergoes a three-stage process to produce spatial stiffness maps that estimates stiffness of biological tissues. First, the application component 101 is adhered to the surface of a human body and the driving component 103 causes the application component 101 to vibrate thereby inducing vibration of the biological tissues under study at a controlled frequency, amplitude, and phase. The MRI scanning system 111 is then used to capture data indicative of the transmitted waves in the region of interest ("ROI"). The wave/vibration data captured by the MRI scanning system 111 is then converted to spatial stiffness maps using a mathematical process called inversion. As described further below, the operation of the driving component 103 is coordinated with the phase of the MRI signal of the MRI scanning system 111. For example, the phase of the tissue vibration is synchronized with the phase of the MRI device to obtain optimal imaging. In some constructions, the MRE system can be used to control when to start imaging with the MRI scanner or vice-versa.

Figure 2:
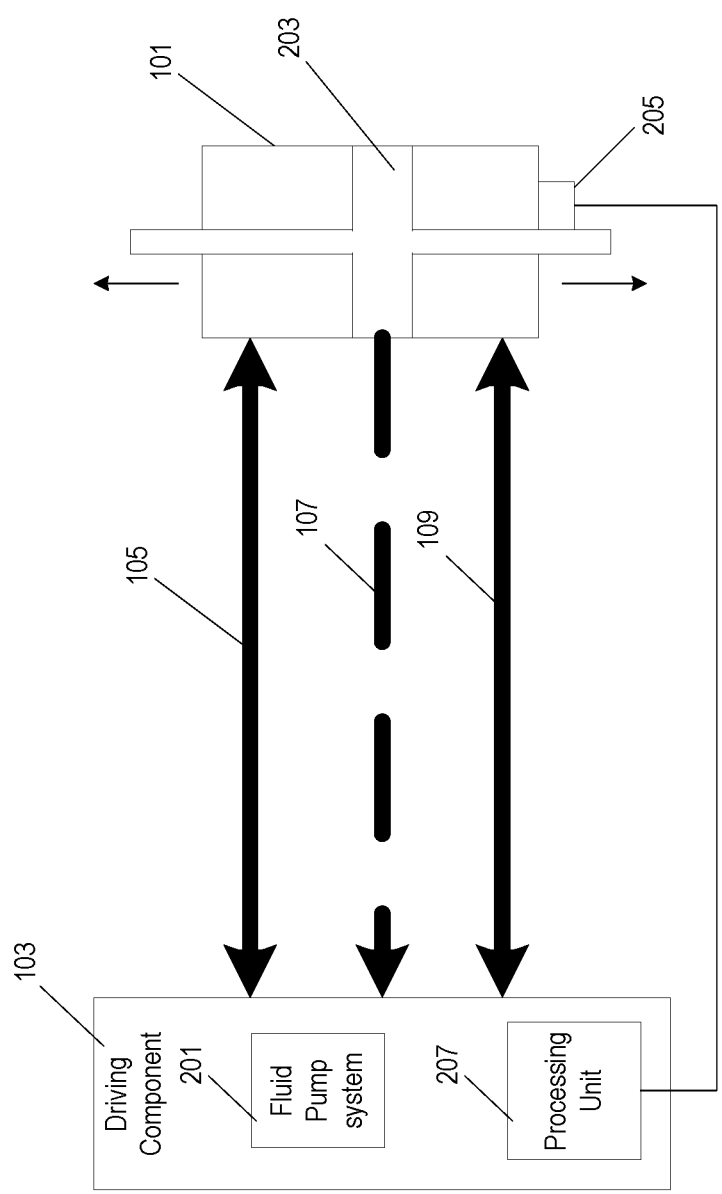
FIG. 2 is a schematic diagram of the drive and actuator components of the system of FIG. 1.

FIG. 2 illustrates the operational components of the hydraulically powered-vibration system in further detail. The driving component 103 includes at least one pump 201 or a combination of a pump and a valve system to provide flow and pressure of a liquid through the plurality of hoses 105, 107, 109 connected to the passive driver 101. The fluid pumped by the driving component 103 into the passive driver 101 causes a piston 203 to move back and forth periodically to induce vibration of the passive driver 101. The pump 201 of the driving component 103 forces fluid into the passive driver 101 through a first hose 105. The increased pressure on one side of the piston 203 causes the piston to move in a first direction (downward in the example of FIG. 2). At the same time, the fluid pump system 201 of the driving component 103 allows fluid on the opposite side of the piston 203 to drain through the second hose 109 as the piston moves.

The passive driver 101 is equipped with a fiber-optic displacement transducer 205 that measures the position of the piston 203 and provides feedback to the processing unit 207 of the driving component 103. Once the piston 203 reaches a defined displacement, the fluid pump system 201 forces fluid into the passive driver 101 through the second hose 109 and allows fluid to drain through the first hose 105. As a result, the piston 203 is moved in the opposite direction (upward in the example of FIG. 2).

Although the example of FIG. 2 includes a displacement sensor 205 that is used to control the operation of the fluid pump system 201, other constructions can utilize other types of sensors to control the operation of the fluid pump system 201. For example, a pressure transducer can be configured to measure the difference in pressure between the first hose 105 and the second hose 109. In the hydraulic system illustrated in FIG. 2, a pressure difference between the two hoses generally correlates to acceleration of the piston. As such, the relative pressures of fluid in the first hose 105 and the second hose 109 and a rate of change of the measured pressure values can be used by the controller to calculated an acceleration of the piston. The fluid pumping system 201 would then be controlled based on these measurements. However, it is noted that, when outside forces are acting on the system (e.g., due to contact with the human body), acceleration is not necessarily a reliable approximation of displacement.

The processing unit 207 of the driving component 103 controls the amplitude of the vibration induced through the passive driver 101 by monitoring the displacement of the piston 203 and causing the fluid pump system 201 to reverse the direction of piston movement when a desired amplitude is reached. The frequency of the vibration is controlled by regulating the speed at which the fluid pump 201 forces the liquid into the passive driver 101.

In some embodiments, the fluid pump system 201 of the driving component 103 includes a conventional hydraulic pump that provides consistent flow and pressure to a four-way electro-hydraulic servo valve ("EHSV") to generate a controlled displacement waveform at the application component 101. The valve is electronically controlled by the processing unit to open in alternating directions of flow to send pressurized hydraulic fluid through either the first hose 105 or the second hose 109 to either side of the piston. In some embodiments, the EHSV includes a conventional nozzle flapper-type electro-hydraulic servo valve. In other constructions, the valve is a voice-coil system. A conventional pump that supplies consistent flow and pressure to piezoelectric liquid valves or a modified pump that supplies timed pulses of flow can also be used to generate a controlled displacement waveform at the application component.

As discussed above, the application component 101, shown in FIG. 2, converts supplied hydraulic flow and pressure into displacement of a moveable surface to cause tissue vibration. The application component may take on various embodiments based on established technologies known to those skilled in the art. These include axial hydraulic actuators, such as a cylinder-piston-rod assembly, or chamber-diaphragm-rod assembly types. Other means of actuation, such as rotary actuators or hydraulic motors, could also be used to devise other embodiments of the application component. In the embodiment shown in FIG. 2, the application component comprises a cylinder with a piston and double-rod assembly. The rod is driven under hydraulic power by the piston such that it reciprocates in a fully-reversed linear motion. The rod, in turn, drives the part of the application component that articulates with the patient to generate a vibrational effect at the surface of the patient's body. It should be clear to those familiar with hydraulic technologies and skilled in the art that this vibrational effect could be generated by hydraulic devices of various constructions and designs. As noted above, the application component 101 in this example is non-metallic (e.g., includes plastic components), which makes it MR compatible. However, in some embodiments, the application component 101 includes at least some metallic components.

As described above, a plurality of hoses distributes a non-compressible liquid between the passive actuator 101 and the driving component 103. Pressurized hydraulic fluid supplied at the first hose 105 moves the piston and rod assembly 203 in the first direction (e.g., downward). Pressurized hydraulic fluid supplied at the second hose 109 moves the piston and rod assembly 203 in the opposite direction (e.g., upward). This motion is transferred to the surface of the passive actuator 101 (for example, by a contact plate as discussed in further detail below) to generate tissue vibrations.

A third hose 107 is a low pressure return hose that allows leakage flow to return to a fluid reservoir of the driving component 103. The return hose 107 also bleeds air from the lines and the cylinder internal volumes. Because the hydraulic systems described in this disclosure benefit from the low-compressibility of the fluid medium, the return hose 107 also bleeds air from the lines and the cylinder internal volumes to remove any trapped air bubbles or "foaming" that may develop in the passive actuator component. As discussed in detail below, the third hose 107 is coupled to the piston housing of the passive actuator 101 such that the piston portion of the piston and rod assembly 203 covers an internal opening to the third hose 107 when the piston is centered. However, when the piston and rod assembly is displaced and reaches the end of its stroke, the internal opening to the third hose 107 is exposed and hydraulic fluid and air is allowed to vent into the low pressure third line 107 from the pressurized cylinder. In this way, any air bubbles are in the cylinder or in the pressurized lines are pushed towards the vent line 107 at the far end of each stroke cycle and released instead of being returned to the hydraulic fluid reservoir.

By using a low-compressible media (e.g., liquid) to drive the passive actuator 101, the hydraulically-powered system provides many advantages over pneumatic means of generating tissue vibration. For example, some pneumatic systems are limited by gas (e.g., air) compliance to a frequency on an order of 100 Hz or less. This frequency limitation limits the resolution of the MRE to the imaging of larger tissue structures. A liquid fluid means of driving the application head does not have this limitation as the media used to convey flow and pressure has relatively low compliance. Therefore, higher transmitted frequencies are possible using the hydraulically-powered vibration device.

In addition, because of the virtual incompressibility of liquids, the performance of the system using the hydraulically-powered vibration device can be predicted with sufficient accuracy to allow the phase of the tissue vibrations to be adjusted to the phase of the applied MRI, which provides optimal imaging. The use of virtually incompressible media also makes it possible to generate higher forces that overcome attenuation of the transmitted energy, which results in the delivery of higher energies to the tissue of interest. Furthermore, because higher power can be transmitted by liquid fluidic means, flexibility in the design of the passive actuator 101 is accommodated. In particular, passive actuators can be implemented that transmit either longitudinal vibrations (i.e., perpendicular to the tissue surface) or shear vibrations (i.e., along the tissue surface). In general, the hydraulically-powered vibration device provides higher-frequency, phase-tuned tissue vibration that provides not only greater imaging resolution due to higher frequency vibration but also better clarity due to phase control.

In some embodiments, the fluid used in the vibration device can be doped with a contrast agent (e.g., super paramagnetic iron oxide) to suppress a signal provided by the fluid in the MRI scanner that can create possible artifacts in the resulting images. Similarly, the field of view can be limited by avoiding the driver or saturation bands that dephase the signal from the fluid to prevent these artifacts. Also, in some embodiments, the passive actuator can be flexible, and can be properly sealed to prevent any fluid leaks.

Figure 3:
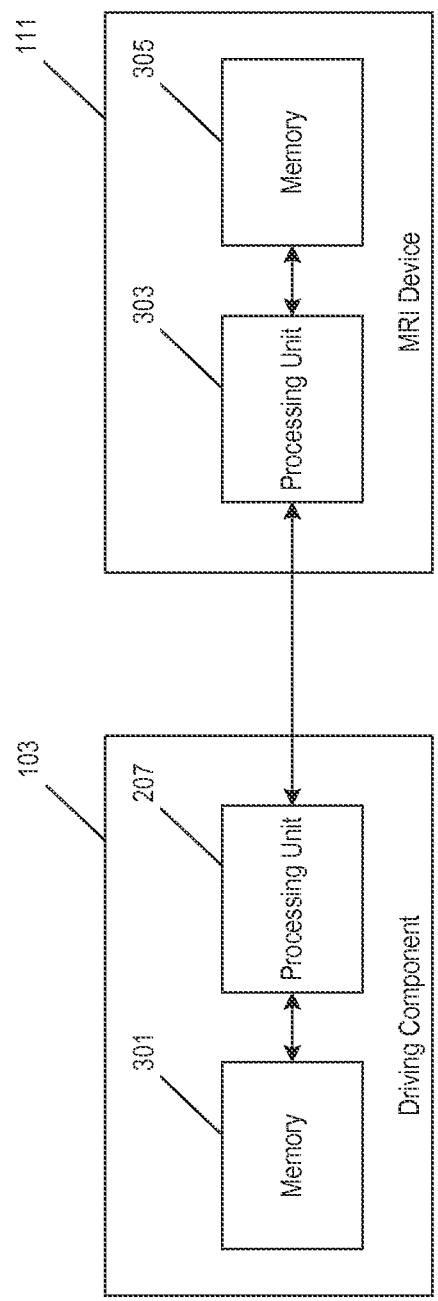
FIG. 3 is a block diagram of a control system for the drive component of FIG. 2 interfacing with a control system for an MRI device.

To further optimize the quality of vibration data acquired by the MRI scanning system 111, the driving component 103 is configured to communication (bidirectional or unidirectional) with the controller of the MRI scanning system 111 as illustrated in FIG. 3. The driving component 103 includes a processing unit (such as a microcontroller) and a memory storing executable instructions and data that, when executed by the processing unit, cause the driving component to operate the fluid pump system and communicate with the MRI scanning system 111. The MRI scanning system also includes a processing unit 303 and a memory 305.

The communication between the driving component 103 and the MRI scanning system 111 allows the vibration to be coordinated with and paced by the pulse sequencing of the MRI scanning system 111 or vice versa. As discussed above, the frequency and amplitude of the induced tissue vibration can be controlled by adjusting the speed at which fluid is pumped into the passive actuator 101 and the desired displacement of the piston and rod assembly 203, respectively. Conversely, in some constructions, the pulse sequencing of the MRI system 111 is controlled based on the frequency and amplitude of the vibrations caused by the driving component 103.

Figure 4A:
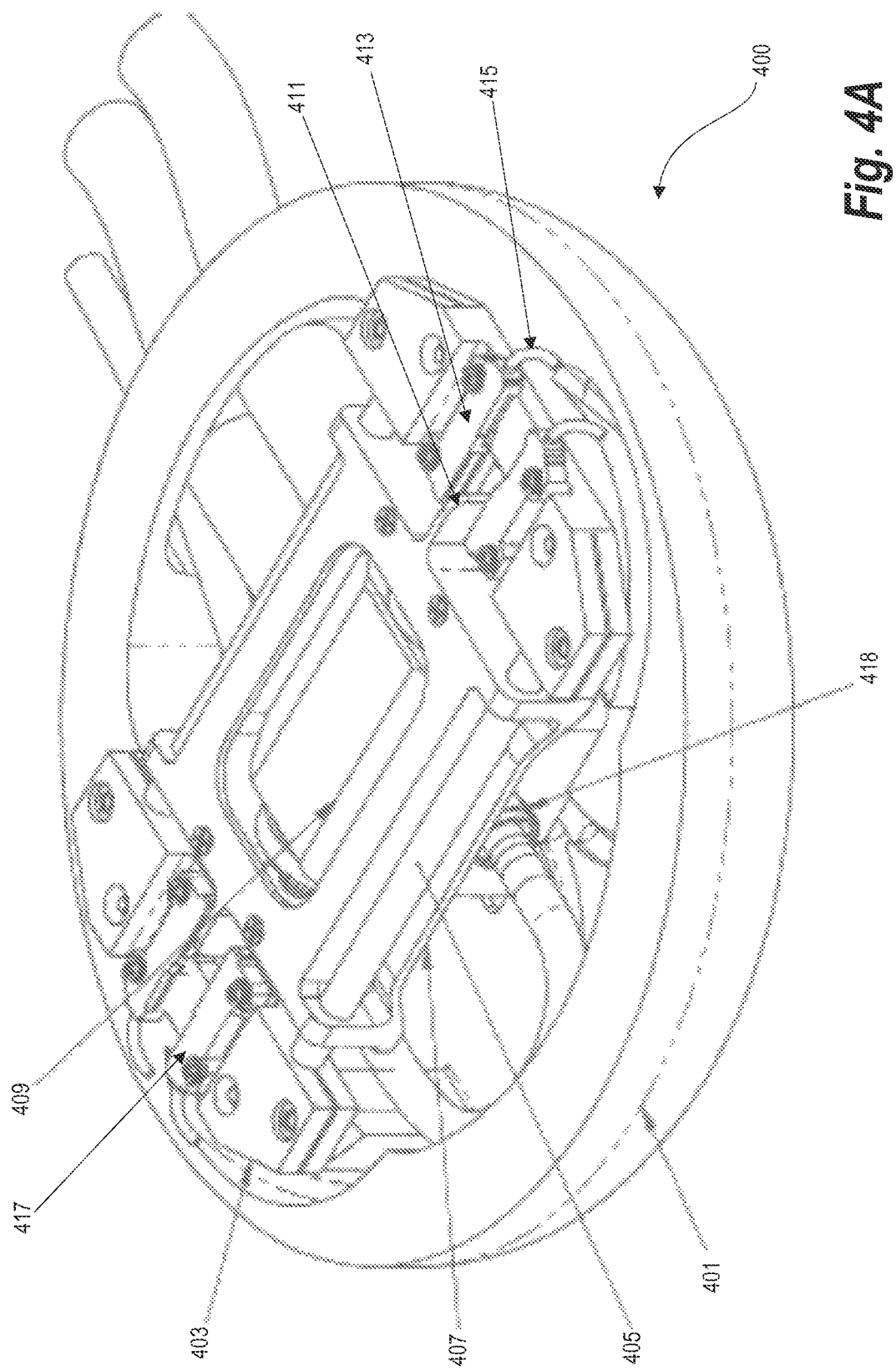
FIG. 4A is a perspective view of one example of a passive actuator component for use in the system of FIG. 1.

FIG. 4A illustrates a more detailed example of a passive hydraulic actuator component 400 for use as the application component 101 in FIG. 1. The actuator component 400 includes a circular-shaped main body 401. Four glide rod mounts 403 are fixedly coupled to the main body 401 and two glide rods 405 are each coupled between one pair of glide rod mounts 403. A shuttle yoke 407 is coupled to the glide rods 405 such that it is linearly slideable along the glide rods 405. The shuttle yoke 407 is fixedly coupled to both ends of a piston rod extending from a piston enclosure 409. The piston enclosure 409 is mounted stationary relative to the main body 401 such that linear reciprocating movement of the piston within the piston enclosure 409 causes the shuttle yoke 407 to move back and forth linearly along the glide rods 405.

Each end of the shuttle yoke 407 includes a protrusion 411 that is positioned to move linearly within a sensor 413 mounted on the glide rod mount 403 on each respective side of the shuttle yoke 407. One side of the sensor 413 is configured to project a linear array of optical signals (e.g., light) which is detected and monitored by fiber optic sensors mounted on the opposite side of the sensor 413. For example, the sensor 413 may include a plurality of light-emitting fibers linearly arranged on one side and one or more light detecting fibers positioned on the opposite side of the sensor 413. As the protrusion 411 of the shuttle yoke 407 advances further into the gap between the two sides of the sensor 413, more and more of the optical signals in the linear array are blocked by the protrusion 411. This blocking is detected by the fiber array on the opposite side of the gap and provide a high-resolution output indicative of the instantaneous displacement of the shuttle yoke 407. The optic signals indicative of the displacement of the shuttle yoke 407 are communicated from the sensor 413 to an external controller through a fiber optic line 415. Furthermore, in the example of FIG. 4A, a second sensor 417 is similarly mounted on the glide rod mounts 403 on the opposite side of the shuttle yoke 407 such that displacement of the shuttle yoke 407 is monitored from both sides. However, in some constructions only a single sensor on one side of the shuttle yoke 407 is used.

Figure 4B:
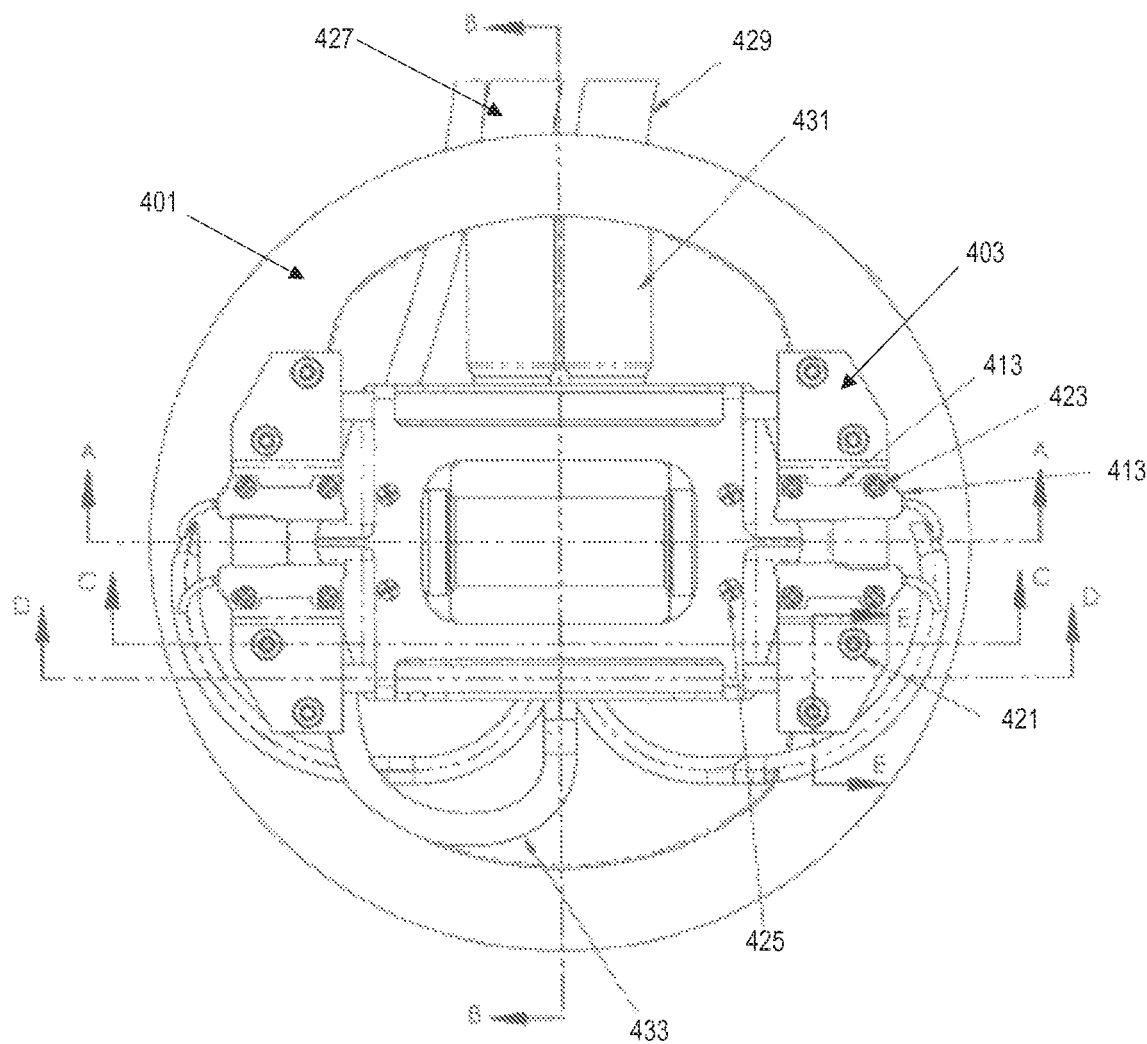
FIG. 4B is an overhead view of the passive actuator component of FIG. 4A.

Three hoses are coupled to the piston enclosure 409 in the actuator component 400. As illustrated in FIG. 4A, a vent line coupling 418 is positioned on a first side of the piston enclosure 409. As illustrated in FIG. 4B, a vent hose 433 is coupled to the vent line coupling 418 to provide for venting of the encased cylinder as described above. A first high pressure hose 427 and a second high pressure hose 429 are also coupled to a hose coupled 431 positioned on the opposite side of the piston enclosure 409. In the example of FIG. 4B, the hoses 427, 429, 433 all extend from the piston enclosure 409 in a direction perpendicular to the axis of movement of the shuttle yoke 407. This positioning prevents pinching of the hoses due to the linear movement of the shuttle yoke 407.

As further illustrated in FIG. 4B, each glide rod mount 403 is coupled to the main body 401 by a pair of flanges 421. Each sensor 413 is coupled to the glide rod mount 403 by a series of screws 423. The shuttle yoke 407 is coupled to each respective end of the piston extending form the piston enclosure 409 by a series of screws 425.

To further describe the details of the actuator component 400, FIGS. 4C, 4D, 4E, 4F, and 4G each provide a cross sectional view of the actuator component. The cross-section of FIG. 4C corresponds to line E-E in FIG. 4B, the cross-section of FIG. 4D corresponds to the line A-A in FIG. 4B, the cross-section of FIG. 4E corresponds to the line C-C in FIG. 4B, the cross-section of FIG. 4F corresponds to the line D-D in FIG. 4B, and the cross-section of FIG. 4G corresponds to the line B-B of FIG. 4B.

Figure 4C:
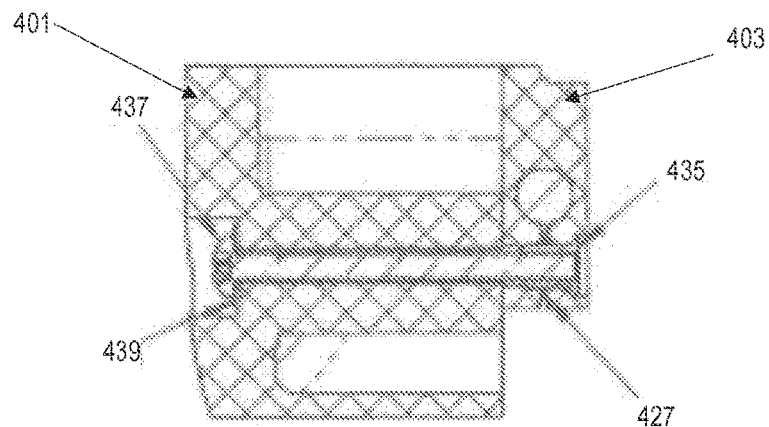
FIG. 4C is a first cross-sectional view of the passive actuator component of FIG. 4A.

FIG. 4C further illustrates the coupling between the glide rod mount 403 and the main body 401. In particular, the flange 427 is held in place on one side by a shim 435. The opposite side is secured by a screw 437 and a washer 439.

Figure 4D:
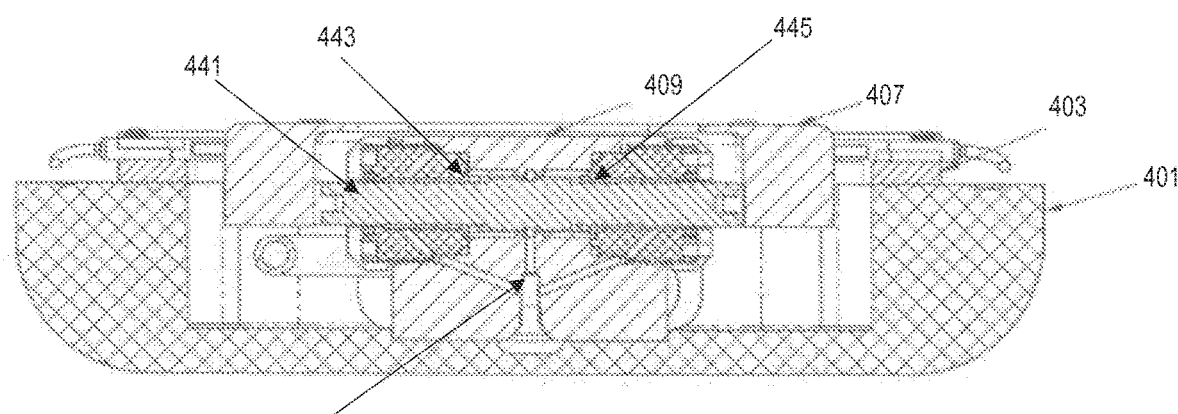
FIG. 4D is a second cross-sectional view of the passive actuator component of FIG. 4A.

FIG. 4D further illustrates the couplings and inner component of the piston enclosure 409. A piston and rod assembly 441 is positioned in the piston enclosure 409. Both ends of the piston and rod assembly 441 extend from the piston enclosure 409 and are coupled to the shuttle yoke 407. The piston enclosure 409 includes internal compartments 443, 445. High pressured hydraulic fluid is alternatingly pumped into and out of these internal compartments on either side of the piston assembly 441 to cause reciprocating movement of the piston and rod assembly 441. For example, fluid is pumped into the enclosure at 443 while pumped from the enclosure at 445 to cause the piston to move to the right of FIG. 4D. Conversely, fluid is pumped into the enclosure at 445 and pumped from the enclosure at 443 to cause the piston to move to the left of FIG. 4D.

The piston enclosure 409 also includes a vent chamber 446. When the piston and rod assembly 441 is in its neutral central position, the opening to the vent chamber 446 is blocked from the internal compartments 443, 445 of the cylinder by the piston and rod assembly 441. When the piston and rod assembly 441 is displaced to the right, the vent chamber 446 is opened to the internal compartment 443 on the left side of the piston 441. Conversely, when the piston and rod assembly 441 is displaced to the left, the vent chamber 446 is opened to the internal compartment 445 on the right side of the piston 441. As discussed above, alternatingly opening the vent chamber 446 to either internal compartment 443, 445 allows hydraulic fluid and any trapped air bubbles (or foam) to be pushed from the cylinder through the low-pressure vent hose 433.

Figure 4E:
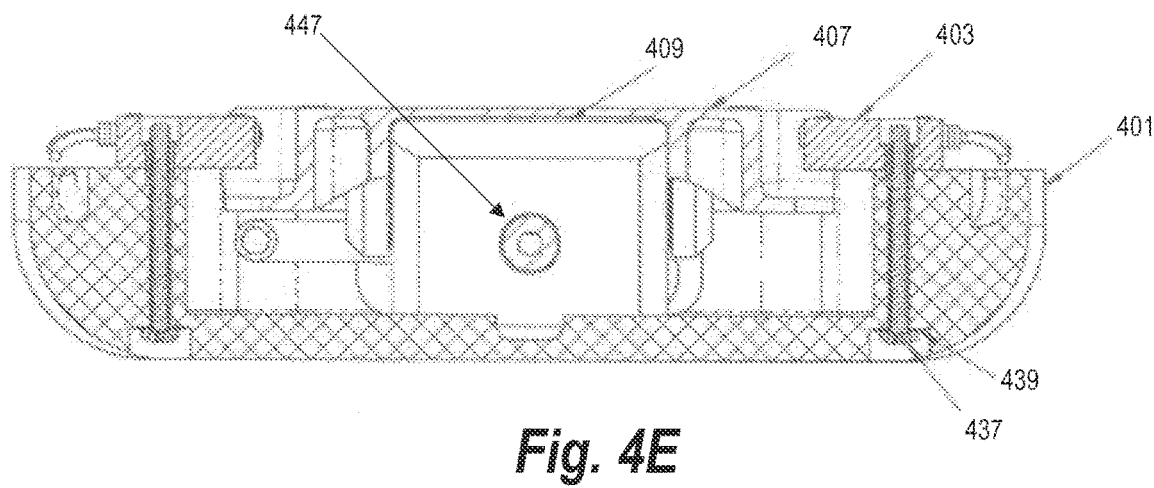
FIG. 4E is a third cross-sectional view of the passive actuator component of FIG. 4A.

FIG. 4E illustrates the opening 447 to the vent chamber 446 for the vent line coupling 418 and FIG. 4F illustrates the placement of the vent line coupling 418. FIG. 4G shows the details of the piston enclosure 409 at a cross-section perpendicular to the piston and rod assembly 441. As shown in FIG. 4G, when temporarily opened by the movement of the piston and rod assembly 441, the vent chamber 446 provides a channel from the cylinder of the piston enclosure 409 through the vent line coupling 418 to the vent hose 433. On the opposite side of the piston enclosure 409, the high pressure lines (including high pressure hose 427) are coupled to the piston enclosure 409.

As discussed above, examples provided in FIGS. 4A-4G illustrate the mechanical inner workings of one example of an actuator component 400. FIG. 5 further illustrates an example of a actuator component including a housing and an interface for translating linear movement of a shuttle yoke into tissue vibration in a patient. Like the example of FIGS. 4A-4G, the actuator component of FIG. 5 includes a piston enclosure 501 fixedly mounted to a main body 503 by a mounting bracket 505. A shuttle yoke 507 is coupled to both ends of a piston rod extending from the piston enclosure 501 and is movably coupled to one or more glide rods 509 such that linear reciprocation of the piston causes corresponding linear movement of the shuttle yoke 507 along the glide rod(s) 509. The glide rod(s) 509 are also fixedly coupled to the main body 503 by a pair of glide rod mounting brackets 511.

A contact plate 513 is coupled to the shuttle yoke 507 and forms an exterior surface of the actuator component of FIG. 5. Due to the coupling, linear movement of the piston causes a corresponding linear reciprocation of both the shuttle yoke 507 and the contact plate 513. To induce tissue vibration in a patient, the actuator component is positioned such that the contact plate 513 is in contact with the tissue of the patient and, through the contact plate 513, linear movement of the piston induces vibration of the tissue.

The main body 503 and other components of the actuator are encased in a housing boot 517. The housing boot 517 is fabricated from a non-metallic material such as injection-molded plastic or another polymeric material and, together with the contact plate, provides the exterior surfaces of the actuator component illustrated in FIG. 5. A flexible gasket 519 coupled to the housing boot 517 (or formed as a component of the housing boot 517) closes the gap between the contact plate 513 and the housing boot 517 while allowing linear reciprocating movement of the contact plate 513 relative to the housing boot 517.

The examples discussed above focus primarily on use of a hydraulic actuator component. However, the actuator components illustrated in FIGS. 4A-4G and FIG. 5 could be adapted to pneumatic mechanisms where pressurized gas is pumped on either side of the piston instead of pressurized fluid. Furthermore, using an application component that is directly operated by hydraulic flow may have drawbacks in certain constructions—particularly when used in an MRI environment. For example, the fluid in hydraulically powered systems is highly pressurized. Manipulating such highly pressured fluid in close proximity to a patient may be undesirable as hydraulic fluid may escape and spill in the event of a rupture of the hydraulic supply lines or in the chambers of the application component. Also, hydraulic drive components are not readily connected and disconnected by the lay person—sophisticated tools and trained professionals may be required to safely replace a hydraulically-driven application component. When a passive hydraulic actuator component is disconnected or replaced, a time-consuming and complicated procedure for purging air from the supply lines and the hydraulic cylinder of the actuator component could be required.

There may also be structural/materials drawbacks associated with a hydraulically-driven application component. Due to the highly pressurized nature of hydraulic fluid, many hydraulic system components are manufactured of a metal material. However, such materials cannot be used for components that are designed to be placed in close proximity or even inside of an MRI system. Such objects would affect the resulting image and may become projectiles when the magnets of the MRI system are activated. Furthermore, the tubes used to transmit pressurized hydraulic fluid are often constructed of a rigid material to prevent rupturing. Such rigid tubing might make it difficult to move the application component to a different location on the body of an imaging subject.

Many of these drawbacks are addressed by a hybrid system that is driven by a hydraulic drive mechanism while also utilizing a pneumatic passive actuator that acts as the application component. A pneumatic actuator would be more easily moved due to the flexible hoses used to transfer pressurized air. A pneumatic actuator could also be move readily removed and replaced by a doctor or other medical professional as it would not require specialized knowledge of hydraulic systems. Furthermore, a pneumatic actuator would be less expensive than a hydraulic application component 101 and could be more easily replaced. For example, a hospital/technician could utilize multiple different passive pneumatic actuator components that are each specialized for different applications. Certain passive actuators could be designed to provide a specific direction of motion or amplitude of vibration. Similarly, individual actuators could be manufactured in various sizes and shapes to accommodate and/or conform to a specific body part. Because the specialized passive actuators in this example are pneumatic, they can be easily and quickly disconnected and replaced without additional specialized equipment or specially trained technicians.

Figure 6:
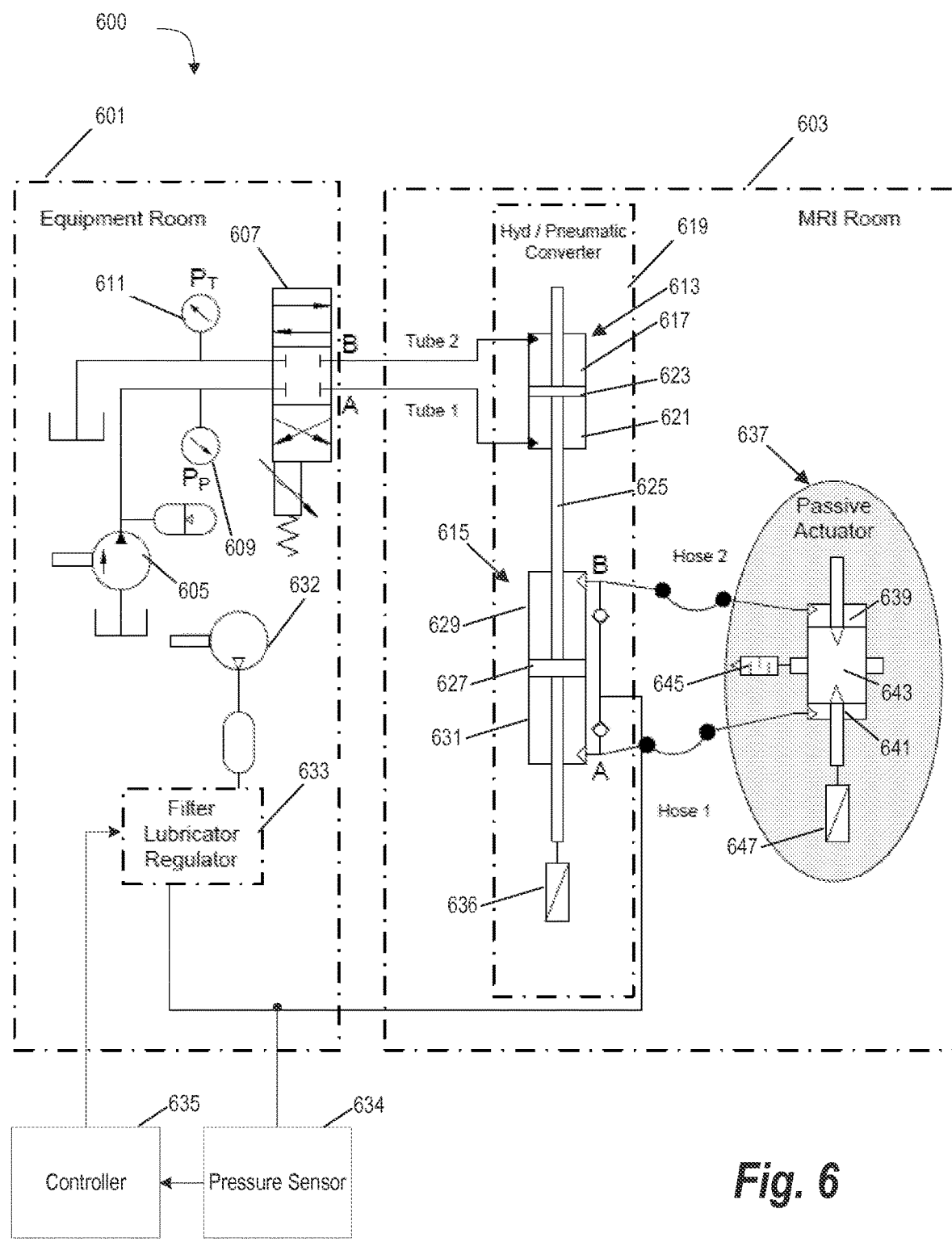
FIG. 6 is a schematic diagram of a hybrid hydraulic-pneumatic drive and actuator system for use in the system of FIG. 1.

FIG. 6 illustrates one example of a hybrid system 600 that utilizes a hydraulically driven system and a passive pneumatic actuator that is placed in contact with the imaging subject. In the example of FIG. 6, the various system components are distributed between an equipment room 601 and the MRI room 603. However, in other constructions, the precise layout and location of the system components may be modified.

Much like the hydraulic system described above, the hybrid system 600 includes a hydraulic pump 605 that provides pressurized fluid to a controlled valve system 607. Fluid pressures are monitored by one or more pressure sensors 609, 611. Pressurized fluid is provided to a hydraulic drive component 613. The hydraulic drive component 613 includes a first chamber 617 and a second chamber 621 separated by a hydraulic piston/diaphragm 623. Although the example of FIG. 6 illustrates only the two high pressure hydraulic lines, in some constructions, the hydraulic drive component 613 will also include a vent line such as discussed above in reference to FIGS. 4A-4G. The valve system 607 alternatingly directs the pressurized fluid to one chamber 617 while allowing fluid to flow out of the other chamber 621. This control mechanism causes the hydraulic piston/diaphragm 621 to move linearly within the hydraulic drive component 613.

The hydraulic drive component 613 is part of a hydraulic/pneumatic converter 619 that also includes a pneumatic drive component 615. The hydraulic piston/diaphragm 613 is fixedly linked to a linear movement stage 625 that is also fixedly coupled to a pneumatic piston/diaphragm 627 that is configured to move linearly within the pneumatic drive component 615. As a result, linear movement of the hydraulic piston/diaphragm 623 translates mechanically to linear movement of the pneumatic piston/diaphragm 627. Like in the hydraulic drive component 613, linear movement of the pneumatic piston/diaphragm 627 changes the relative volume of a first pneumatic chamber 629 and a second pneumatic chamber 631 located within the pneumatic drive component 615 on either side of the pneumatic piston/diaphragm 623. An air compressor 632 and a filter/lubricator/regulator module 633 located in equipment room 601 operate to maintain a consistent and controllable minimum air pressure within the pneumatic drive component 615. A pressure sensor 634 monitors the pressure in the filter/lubricator/regulator module 633 and a controller 635 controls the operation of the filter/lubricator/regulator module 633 based in part on the measured pressure.

A displacement sensor 636, such as, for example, the fiber optic displacement sensor 413 of FIG. 4A is positioned to monitor the linear position of the linear movement stage 625. This displacement signal is provided as feedback to a controller (not pictured) that operates the controlled valve system 607 and the hydraulic pump 605 to regulate the operation of the MRE system 600. Although the displacement sensor 636 is shown in FIG. 6 coupled to the linear movement stage 625 on the side opposite the pneumatic piston/diaphragm 627, in other constructions, the displacement sensor many be positioned and configured to monitor movement of the linear movement stage 625 between the hydraulic drive mechanism 613 and the pneumatic drive mechanism 615. Similarly, some other construction may not even include a rod portion extending beyond the pneumatic piston/diaphragm 627 or the hydraulic piston/diaphragm 623 and instead only include a rod portion 625 coupling the hydraulic piston/diaphragm 623 to the pneumatic piston/diaphragm 627.

The pneumatic drive component 615 is coupled to a passive pneumatic actuator 637 by a pair of hoses (Hose 1 and Hose 2) that are manufactured of a non-metallic material such as, for example, plastic or another polymeric material. Hose 2 couples the first chamber 629 of the pneumatic drive component to a first chamber 639 of the passive actuator. Similarly, Hose 1 couples the second chamber 631 of the pneumatic drive component to a second chamber 641 of the passive actuator. The first chamber 639 and the second chamber 641 of the passive actuator are separated by a piston stage 643 that moves linearly inside the passive actuator 637.

Therefore, the valve system 607 controls the flow of pressurized fluid to and from the first chamber 617 and the second chamber 621 of the hydraulic drive component 613. This alternating flow of fluid causes linear reciprocation of the linear movement stage 625, which, in turn, causes alternating linear movement of the pneumatic piston/diaphragm component 627 within the pneumatic drive component 615. Although an overall air pressure is maintained with in the pneumatic system by the compressor 633, linear movement of pneumatic piston/diaphragm component 627 forces air through either Hose 1 or Hose 2 and increases the air pressure in either the first chamber 639 or the second chamber 641 of the passive actuator 637. This increased air pressure causes linear movement of the piston stage 643 within the passive actuator 637. The alternating linear movement of the piston stage 643 induces vibration of the anatomical tissue of the imaging subject.

In some constructions, the pneumatic drive component 615 is operated by compressed nitrogen while, in other constructions, compressed air is used. However, in still other components, other type of compressed gas may be used to drive the pneumatic component of the system 600.

In the example illustrated in FIG. 6, the passive actuator 637 is either controllably or automatically mechanically vented. For example, a displacement sensor 647 is positioned to monitor the linear position/displacement of the piston stage 643. When the signal from the displacement sensor 647 indicates that the piston stage 643 has reached its target displacement, venting mechanism 645 is controllably opened to release pressurized air and a signal is sent to the controller (not pictured) to alternate the direction of hydraulic fluid pumping. Alternatively, the valve 645 may be positioned such that the opening is blocked by the piston stage 643 itself until a target displacement is reached—at which time, the valve opening is exposed and pressurized air is released (similar to the operation of the venting chamber 446 discussed above in reference to FIGS. 4A-4G).

Due to this mechanical venting, pressurized air does not need to return to the pneumatic drive component 615 through Hose 1 or Hose 2 when the direction of linear movement changes. Instead, the compressor 633 and the filter/lubricator/regulator module 635 operates to compensate for the released air and maintains a substantially constant minimum air pressure within the pneumatic system. However, some alternative constructions may implement a closed pneumatic system where gas is pumped back into the pneumatic drive component 615 when the linear direction of the piston stage 643 changes.

Furthermore, although the example discussed above in FIGS. 4A-4G is described above as a hydraulic actuator component, the same or similar structure could be implemented as the passive pneumatic actuator 637 in a hybrid hydraulic/pneumatic system 600 where the vent chamber 446 is replaced or augmented to operate as the venting mechanism 645.

In the hybrid system 600, frequency of tissue vibration is varied by controlling the frequency at which the linear movement stage 625 changes direction. This movement is controlled, in turn, by varying the operation of the valve system 607 to control the frequency at which the system changes from pumping fluid through Tube 1 and drawing fluid back though Tube 2 to pumping fluid through Tube 2 and drawing fluid back through Tube 1.

The amplitude of induced tissue vibration in the hybrid system 600 may be adjusted by controlling the total displacement of the hydraulic piston/diaphragm 623, for example, by varying the speed at which the fluid is pumped into the hydraulic drive component 613. However, in constructions where air is vented from the passive pneumatic actuator based on displacement position of the piston stage 643, amplitude of the induced vibration may additionally be controlled by changing the displacement where mechanical venting occurs. This may be implemented, for example, by providing a mechanism by which the physical location of the vent opening is moved to tune the vibration amplitude or my adjusting a "trigger point" where the valve is opened to vent air from either the first chamber 639 or the second chamber 641.

Thus, the invention provides, among other things, a hydraulic system and a hybrid hydraulic-pneumatic system for inducing vibrations in target tissue so that spatial stiffness maps can be generated using magnetic resonance elastography. Various features and advantages of the invention are set forth in the following claims.

What is claimed is:

1. A system for inducing tissue vibration for magnetic resonance elastography, the system comprising:
    a hydraulic-to-pneumatic converter including
        a linearly reciprocating hydraulic piston at least partially enclosed in a hydraulic piston enclosure,
        a linearly reciprocating pneumatic piston at least partially enclosed in a first pneumatic piston enclosure, and
        a linear movement stage fixedly coupled to the hydraulic piston and the pneumatic piston such that linear movement of the hydraulic piston causes a corresponding linear movement of the pneumatic piston;
    a hydraulic drive component configured to alternatingly pump hydraulic fluid into the hydraulic piston enclosure on a first side of the hydraulic piston to cause the hydraulic piston to move in a first linear direction and on a second side of the hydraulic piston to cause the hydraulic piston to move in a second linear direction, the second linear direction being opposite the first linear direction; and
    a passive pneumatic actuator component positionable proximate to a target tissue, the passive pneumatic actuator component including a second linearly movable pneumatic piston at least partially enclosed in a second pneumatic piston enclosure, the second pneumatic piston enclosure being pneumatically coupled to the first pneumatic piston enclosure such that movement of the first pneumatic piston in the first linear direction due to movement of the hydraulic piston causes corresponding movement of the second pneumatic piston in a first linear direction and movement of the first pneumatic piston in the second linear direction due to movement of the hydraulic piston causes corresponding movement of the second pneumatic piston in a second linear direction.

2. The system of claim 1, wherein the hydraulic drive component further includes
    a fluid pump,
    a controllable valve system,
    a first hydraulic supply line,
    a second hydraulic supply line, and
    a controller configured to operate the controllable valve system to alternatingly
        pump fluid through the first hydraulic supply line into the hydraulic piston enclosure on a first side of the hydraulic piston while drawing fluid from the hydraulic piston enclosure on the second side of the hydraulic piston through the second hydraulic supply line and
        pump fluid through the second hydraulic supply line into the hydraulic piston enclosure on the second side of the hydraulic piston while drawing fluid from the hydraulic piston enclosure on the first side of the hydraulic piston through the first hydraulic supply line.

3. The system of claim 2, wherein the hydraulic-to-pneumatic converter further includes a displacement sensor configured and positioned to monitor a displacement of the linear movement stage, wherein the displacement sensor is communicatively coupled to the controller of the hydraulic drive component, and
    wherein the controller of the hydraulic drive component is further configured to operate the controllable valve system to alternate the pumping of fluid based on the output of the displacement sensor.

4. The system of claim 3, wherein the displacement sensor includes a fiber optic transducer that is partially obstructed by a linearly moving component in proportion to the displacement of the first pneumatic piston.

5. The system of claim 2, wherein the passive pneumatic actuator further includes a displacement sensor configured and positioned to monitor displacement of the second pneumatic piston, wherein the displacement sensor is communicatively coupled to the controller of the hydraulic drive component, and
    wherein the controller of the hydraulic drive component is further configured to operate the controllable valve system to alternate the pumping of fluid based on the output of the displacement sensor.

6. The system of claim 2, wherein the hydraulic-to-pneumatic converter further includes a vent channel coupled to the hydraulic piston enclosure and positioned such that
    the vent channel is closed by the hydraulic piston during at least a portion of the linear movement of the hydraulic piston,
    the vent channel is open to the hydraulic piston enclosure on a first side of the hydraulic piston when the hydraulic piston is displaced in a first direction opposite the first side of the hydraulic piston, and
    the vent channel is open to the hydraulic piston enclosure on the second side of the hydraulic piston when the hydraulic piston is displaced in a second direction opposite the second side of the hydraulic piston, wherein the vent channel is configured to allow gas trapped in the hydraulic piston enclosure to vent through the low pressure vent channel when high pressure fluid is pumped into the hydraulic piston enclosure.

7. The system of claim 1, wherein the pneumatic drive component further includes a pneumatic gas compressor pump coupled to the pneumatic piston enclosure of the hydraulic-to-pneumatic converter, wherein the pneumatic gas compressor pump is configured to maintain a substantially constant minimum pneumatic gas pressure within the pneumatic piston enclosure.

8. The system of claim 1, further comprising a first hose pneumatically coupled to the first pneumatic piston enclosure of the hydraulic-to-pneumatic converter on a first side of the first pneumatic piston and pneumatically coupled to the second pneumatic piston enclosure of the pneumatic actuator on a first side of the second pneumatic piston such that linear movement of the pneumatic piston stage towards the first side of the first pneumatic piston forces pneumatic gas from the first pneumatic piston enclosure of the hydraulic-to-pneumatic converter through the first hose and into the second pneumatic piston enclosure of the pneumatic actuator on the first side of the second pneumatic piston, and wherein forcing pneumatic gas into the second pneumatic piston enclosure on the first side of the second pneumatic piston causes the second pneumatic piston to move in a linear direction opposite the first side of the actuator piston assembly.

9. The system of claim 8, wherein the passive actuator component further includes a mechanical valve configured to release pneumatic gas from the actuator housing when a defined displacement of the actuator piston assembly is achieved.

10. The system of claim 1, wherein the linear movement stage is fixedly and concentrically linked to both the hydraulic piston and the first pneumatic piston such that linear movement of the hydraulic piston stage in the first direction relative to the hydraulic piston enclosure causes linear movement of both the linear movement stage and the first pneumatic piston in the same linear direction.

11. The system of claim 1, wherein the second pneumatic piston of the pneumatic actuator is coupled to a contact plate, and wherein, when the contact plate is placed in contact with a target tissue of a patient, the alternating linear movement of the contact plate caused by the alternating linear movement of the second pneumatic piston induces vibration of the target tissue of the patient.

12. The system of claim 1, wherein the pneumatic actuator is constructed of only non-metallic and non-ferromagnetic materials.

13. The system of claim 1, wherein the pneumatic actuator is positionable within an MM environment and wherein the hydraulic drive component is positioned in a room outside of the MRI environment.

14. The system of claim 1, wherein the hydraulic drive component is configured to adjust a frequency of induced tissue vibration by adjusting a speed at which the fluid is pumped to the hydraulic piston enclosure.

15. The system of claim 1, wherein the pneumatic actuator component is positionable on a skin surface of a patient to induce vibration such that the first linear direction of the pneumatic actuator component is parallel to a skin surface of a patient.

16. A method of inducing tissue vibration for magnetic resonance elastography, the method comprising:
positioning a passive actuator component on an imaging subject proximate to a target tissue, the passive actuator component including a linearly movable actuator piston assembly enclosed in an actuator housing; and
alternatingly pumping fluid into a hydraulic drive housing on a first side of a hydraulic piston assembly and on a second side of the hydraulic piston assembly, wherein pumping fluid into the hydraulic drive housing on the first side of the hydraulic piston assembly causes the hydraulic piston assembly to move in a linear direction opposite the first side of the hydraulic piston assembly, wherein pumping fluid into the hydraulic drive housing on the second side of the hydraulic piston assembly causes the hydraulic piston assembly to move in a linear direction opposite the second side of the hydraulic piston assembly, wherein a mechanical linkage between the hydraulic piston assembly and a pneumatic piston assembly positioned within a pneumatic drive housing causes the pneumatic piston assembly to move in a first linear direction relative to the pneumatic drive housing in response to linear movement of the hydraulic piston assembly in the linear direction opposite the first side of the hydraulic piston assembly, wherein the mechanical linkage causes the pneumatic piston assembly to move in a second linear direction relative to the pneumatic drive housing in response to linear movement of the hydraulic piston assembly in the linear direction opposite the second side of the hydraulic piston assembly, wherein a pneumatic linkage between the pneumatic drive housing and the passive actuator component causes a pneumatic gas to be forced from the pneumatic drive housing on a first side of the pneumatic piston stage into the actuator housing on a first side of the actuator piston assembly in response to movement of the pneumatic piston stage in the first linear direction relative to the pneumatic drive housing, wherein the pneumatic linkage causes the pneumatic gas to be forced from the pneumatic drive housing on a second side of the pneumatic piston stage into the actuator housing on a second side of the actuator piston assembly in response to movement of the pneumatic piston stage in the second linear direction relative to the pneumatic drive housing, wherein forcing the pneumatic gas into the actuator housing on the first side of the actuator piston assembly causes the actuator piston assembly to move in a linear direction opposite the first side of the actuator piston, and wherein forcing the pneumatic gas into the actuator housing on the second side of the actuator piston assembly causes the actuator piston assembly to move in a linear direction opposite the second side of the actuator piston.

17. The method of claim 16, further comprising adjusting a frequency of alternating linear movement of the actuator piston assembly within the actuator housing by adjusting a speed at which the fluid is pumped into the hydraulic drive housing.

18. The method of claim 16, further comprising adjusting a frequency of induced tissue vibration by adjusting a speed at which the fluid is pumped into the hydraulic drive housing.

* * * * *